United States Patent
Lee et al.

(10) Patent No.: US 9,192,358 B2
(45) Date of Patent: Nov. 24, 2015

(54) METHOD AND APPARATUS FOR GUIDING SCAN LINE BY USING COLOR DOPPLER IMAGE

(71) Applicant: SAMSUNG MEDISON CO., LTD., Gangwon-do (KR)

(72) Inventors: Bong-heon Lee, Gangwon-do (KR); Jin-yong Lee, Gangwon-do (KR)

(73) Assignee: SAMSUNG MEDISON CO., LTD., Hongcheon-Gun, Gangwon-Do (KR)

( * ) Notice: Subject to any disclaimer, the term of this patent is extended or adjusted under 35 U.S.C. 154(b) by 240 days.

(21) Appl. No.: 13/919,709

(22) Filed: Jun. 17, 2013

(65) Prior Publication Data

US 2014/0081143 A1     Mar. 20, 2014

(30) Foreign Application Priority Data

Sep. 18, 2012   (KR) .................. 10-2012-0103612

(51) Int. Cl.
| | |
|---|---|
| *A61B 8/08* | (2006.01) |
| *A61B 8/06* | (2006.01) |
| *A61B 8/00* | (2006.01) |
| *G01S 15/89* | (2006.01) |
| *G01S 7/52* | (2006.01) |

(52) U.S. Cl.
CPC . *A61B 8/488* (2013.01); *A61B 8/06* (2013.01); *A61B 8/463* (2013.01); *A61B 8/54* (2013.01); *G01S 7/5205* (2013.01); *G01S 7/52085* (2013.01); *G01S 15/8979* (2013.01); *A61B 8/469* (2013.01)

(58) Field of Classification Search
CPC .......... A61B 8/06; A61B 8/463; A61B 8/469; A61B 8/488; A61B 8/54; G01S 15/8979; G01S 7/5205; G01S 7/52088
See application file for complete search history.

(56) References Cited

U.S. PATENT DOCUMENTS

| | | | |
|---|---|---|---|
| 5,709,211 | A | 1/1998 | Machida |
| 6,068,598 | A | 5/2000 | Pan et al. |
| 6,464,641 | B1 | 10/2002 | Pan et al. |
| 7,578,792 | B2 | 8/2009 | Lee et al. |
| 7,766,836 | B2 | 8/2010 | Waki |

FOREIGN PATENT DOCUMENTS

| | | |
|---|---|---|
| EP | 0 033 977 A2 | 8/1981 |
| EP | 1 152 364 A2 | 11/2001 |
| JP | 2000-139921 A | 5/2000 |
| JP | 2000-287977 A | 10/2000 |
| JP | 2011-010789 A | 1/2011 |
| WO | 2006/073088 A1 | 7/2006 |

OTHER PUBLICATIONS

Extended European Search Report issued in European Patent Application No. EP 13164035.1 dated Jul. 23, 2013.
Korean Office Action issued in Application No. 10-2012-0103612 dated Jul. 1, 2014.
Korean Notice of Notice of Allowance issued in counterpart Korean Patent Application No. 10-2012-0103612 on Dec. 23, 2014; 8 pages with English translation.

*Primary Examiner* — Michael Rozanski
(74) *Attorney, Agent, or Firm* — McDermott Will & Emery LLP (57) ABSTRACT

Provided are a method and apparatus for guiding a scan line. The method includes: detecting a bloodstream region indicating a flow of blood from a color Doppler image; determining a central axis of the bloodstream region; measuring an angle between the central axis and a scan line used to obtain the color Doppler image; and displaying the angle on a screen.

18 Claims, 6 Drawing Sheets

METHOD AND APPARATUS FOR GUIDING SCAN LINE BY USING COLOR DOPPLER IMAGE

CROSS-REFERENCE TO RELATED PATENT APPLICATION

This application claims the benefit of Korean Patent Application No. 10-2012-0103612, filed on Sep. 18, 2012, in the Korean Intellectual Property Office, the disclosure of which is incorporated herein in its entirety by reference.

BACKGROUND OF THE INVENTION

1. Field of the Invention

The present invention relates to an apparatus and method of diagnosing an object by using ultrasound waves, and more particularly, to a method and apparatus for guiding an angle of a scan line along which an object is scanned.

2. Description of the Related Art

An ultrasonic diagnostic apparatus generates an ultrasonic signal (with a frequency equal to or greater than about 20 kHz in general) by using a probe for a predetermined portion inside an object, and obtains an image of the predetermined portion inside the object by using information about a reflected echo signal. In particular, an ultrasonic diagnostic apparatus is medically used to detect foreign materials inside an object, measure a damage of the object, and examine the interior parts of the object. Such an ultrasonic diagnostic apparatus is widely used along with other imaging diagnostic apparatuses because the ultrasonic diagnostic apparatus has higher stability than an X-ray-based diagnostic apparatus, displays an image in real time, and has no risk of radiation exposure.

An image obtained by an ultrasonic diagnostic apparatus (hereinafter, referred to as an ultrasound image) may be displayed on the ultrasonic diagnostic apparatus, or may be stored in a storage medium and displayed on another image display apparatus. For example, an ultrasound image may be reduced in size and then may be displayed on a screen of, for example, a mobile phone, a portable electronic device, a personal digital assistant (PDA), or a tablet personal computer (PC).

SUMMARY OF THE INVENTION

The reliability of a color Doppler image varies according to an angle between a scan line along which an image is scanned and a direction of a bloodstream. Accordingly, it is necessary to minimize the angle between the scan line and the direction of the bloodstream.

The present invention provides a method and apparatus for guiding an angle of a scan line by using a color Doppler image. The present invention also provides a computer-readable recording medium having embodied thereon a program for executing the method.

According to an aspect of the present invention, there is provided a method of guiding a scan line by using a color Doppler image, the method including: detecting a bloodstream region indicating a flow of blood from the color Doppler image; determining a central axis of the bloodstream region; measuring an angle between the central axis and the scan line used to obtain the color Doppler image; and displaying the angle on a screen.

The measuring of the angle may include: displaying the central axis and the scan line on the screen; and measuring the angle between the central axis and the scan line on the screen.

The displaying of the angle on the screen may include changing a color of the angle displayed on the screen according to whether the angle is within a predetermined range.

The determining of the central axis may include determining as the central axis a straight line whose length is the greatest from among straight lines obtained by connecting arbitrary points included in the bloodstream region.

The determining of the central axis may include determining as the central axis a straight line whose length included in the bloodstream region is the greatest from among a plurality of straight lines passing through a central point of the bloodstream region.

The detecting of the bloodstream region may include detecting the bloodstream region by using color information of one or more color regions included in the color Doppler image.

The detecting of the bloodstream region may include: obtaining an average color value of the one or more color regions by using color values of a plurality of pixels included in each of the one or more color regions; and detecting as the bloodstream region a color region whose velocity is within a predetermined range from among the one or more color regions included in the color Doppler image.

The detecting of the bloodstream region may include receiving a user input that selects a predetermined region included in the color Doppler image, and detecting the predetermined region as the bloodstream region.

The method may further include outputting an alarm message when the angle is not within a predetermined range.

According to another aspect of the present invention, there is provided an apparatus for guiding a scan line by using a color Doppler image, the apparatus including: an image analyzing unit that detects a bloodstream region indicating a flow of blood from the color Doppler image; a central axis determining unit that determines a central axis of the bloodstream region; an angle measuring unit that measures an angle between the central axis and the scan line used to obtain the color Doppler image; and a display unit that displays the angle on a screen.

According to another aspect of the present invention, there is provided a computer-readable recording medium having embodied thereon a program for executing the method.

BRIEF DESCRIPTION OF THE DRAWINGS

The above and other features and advantages of the present invention will become more apparent by describing in detail exemplary embodiments thereof with reference to the attached drawings in which reference numerals denote structural elements and.

DETAILED DESCRIPTION OF THE INVENTION

Expressions such as "at least one of," when preceding a list of elements, modify the entire list of elements and do not modify the individual elements of the list.

Most of the terms used herein are general terms that have been widely used in the technical art to which the present invention pertains. However, some of the terms used herein may be created reflecting intentions of technicians in this art, precedents, or new technologies. Also, some of the terms used herein may be arbitrarily chosen by the present applicant. In this case, these terms are defined in detail below. Accordingly, the specific terms used herein should be understood based on the unique meanings thereof and the whole context of the present invention.

In the present specification, it should be understood that the terms, such as 'including' or 'having' are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added. Also, the terms, such as 'unit' or 'module' should be understood as a unit that processes at least one function or operation and that may be embodied in a hardware manner, a software manner, or a combination of the hardware manner and the software manner.

The present invention will now be described more fully with reference to the accompanying drawings, in which exemplary embodiments of the invention are shown.

Figure 1:
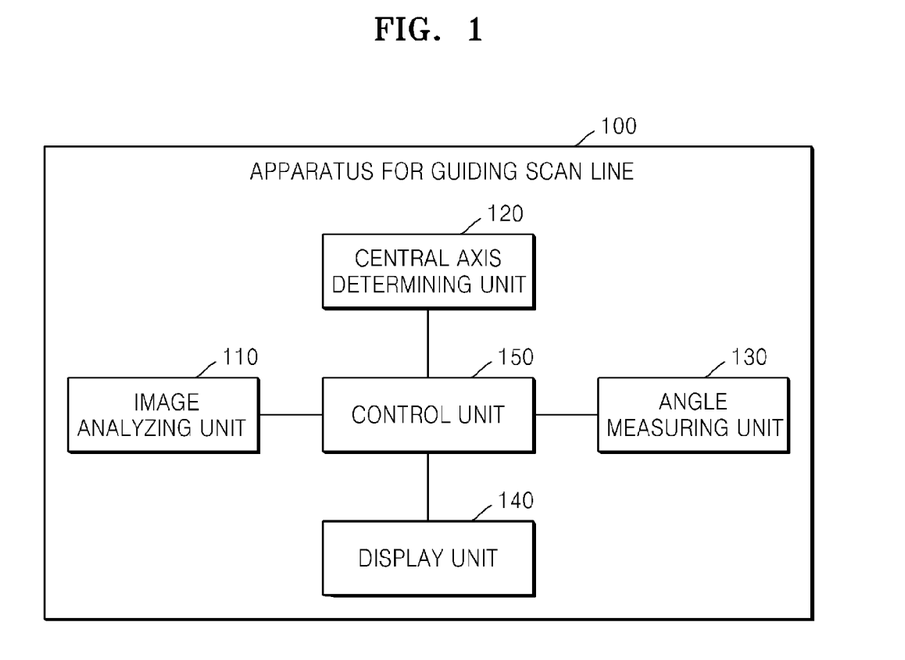
FIG. 1 is a block diagram illustrating an apparatus for guiding a scan line, according to an embodiment of the present invention.

FIG. 1 is a block diagram illustrating an apparatus 100 for guiding a scan line, according to an embodiment of the present invention. The apparatus 100 may include an image analyzing unit 110, a central axis determining unit 120, an angle measuring unit 130, a display unit 140, and a control unit 150. The apparatus 100 may further include general-purpose elements other than the elements shown in FIG. 1.

The apparatus 100 emits an ultrasonic signal to an object, receives an echo signal reflected from the object, and generates an ultrasound image. Also, the apparatus 100 displays the ultrasound image generated by processing received data on a screen, thereby enabling a user to diagnose the object. That is, the apparatus 100 may be an ultrasonic diagnostic apparatus that scans an object, generates an ultrasound image, and outputs the ultrasound image.

The apparatus 100 may obtain a color Doppler image by scanning an object. The color Doppler image is an image showing a velocity, at which a bloodstream of the object flows, in a color. That is, the color Doppler image is obtained in a color Doppler mode in which a scan line along which the object is scanned is moved, an ultrasonic signal is emitted for every scan line a predetermined number of times or more, and an echo signal is received. Data obtained in the color Doppler mode is matched to a color value for respective pixels by using a color map that matches a velocity of a measured bloodstream and a color value and is output in a color.

Also, when the apparatus 100 obtains the color Doppler image that shows a velocity of a bloodstream in a color, a predetermined angle (hereinafter, referred to as a Doppler angle) is formed between a direction in which an ultrasonic signal is output from the apparatus 100 and a direction in which blood flows. The Doppler angle affects reliability of the color Doppler image obtained by the apparatus 100. For example, when the direction in which the ultrasonic signal is output is the same as the direction in which the blood flows (that is, when the Doppler angle is 0°), the velocity of the bloodstream may be accurately measured. On the contrary, the angle between the direction in which the ultrasonic signal is output and the direction in which the blood flows is 90° (that is, when the Doppler angle is 90°), the velocity of the bloodstream may not be measured. Accordingly, in order to obtain a reliable image, a user of the ultrasonic diagnostic apparatus 100 needs to minimize the Doppler angle when scanning the object.

Elements included in the apparatus 100 of FIG. 1 will now be explained in detail.

The image analyzing unit 110 detects a bloodstream region indicating a flow of blood from the color Doppler image. The color Doppler image may include one or more regions which are shown in colors according to a velocity at which the object in the color doppler image moves. That is, the color Doppler image may include one or more color regions which are shown in different colors. The image analyzing unit 110 detects a bloodstream region from among the one or more regions included in the color Doppler image.

The image analyzing unit 110 may detect a bloodstream region from the color Doppler image previously stored in a storage unit 170 (see FIG. 2) of the apparatus 100 or from the color Doppler image obtained by scanning the object in real time.

A color value is matched to a velocity at which each of the one or more regions included in the color Doppler image obtained by scanning the object moves. The apparatus 100 may filter velocities of the one or more regions obtained by scanning the object and may match a color value to a region whose velocity is matched to a velocity of a bloodstream to be measured. Accordingly, the color Doppler image may include not only a color region but also a black-and-white region which has only brightness. That is, the color Doppler image may include both a color region which corresponds to a bloodstream and a black-and-white region which does not correspond to the bloodstream.

The image analyzing unit 110 may detect a bloodstream region by using color information of one or more color regions included in the color Doppler image. In detail, each of the color regions may include a plurality of pixels to which color values are matched, and the image analyzing unit 110 may detect a bloodstream region by using the color values of the color regions.

Since a color value in the color Doppler image indicates a velocity at which the object moves, the image analyzing unit 110 may detect a bloodstream region by using a velocity at which a region included in the color Doppler image moves (that is, a velocity shown in a color on a screen).

For example, the image analyzing unit 110 may obtain an average color value of a plurality of pixels included in a color region and may detect as a bloodstream region a color region whose average color value is within a predetermined range. That is, the image analyzing unit 110 may detect as a bloodstream region a color region whose color value is within a range of color values (that is, color values indicating velocities) which has been previously stored for a portion to be measured from among one or more color regions.

Alternatively, the image analyzing unit 110 may detect a color region from among one or more color regions included in the color Doppler image by using information about a color value matched to a velocity of a bloodstream which has been previously input to the apparatus 100.

For example, when a backward flow of blood in a valve is measured, a user may know a direction in which the blood flows, and may know in advance a velocity at which the blood flows backward. Accordingly, the image analyzing unit 110 may detect as a bloodstream region a color region displayed on the color Doppler image by using a color value matched to a velocity and a direction of a bloodstream which has been previously stored. The present embodiment will be described later in detail with reference to FIG. 5.

Alternatively, when one color region is included in the color Doppler image, the image analyzing unit 110 may simply detect a color region with a color value as a bloodstream region.

Although the image analyzing unit 110 automatically detects a bloodstream region in the above, the image analyzing unit 110 may manually detect a bloodstream region according to a user input. That is, the apparatus 100 may further include a user input unit 190 (see FIG. 2), and the image analyzing unit 110 may detect a bloodstream region by using the user input unit 190 that selects a predetermined region included in the color Doppler image.

In detail, when the apparatus 100 displays the color Doppler image, the user may select a predetermined region in the color Doppler image displayed on a screen by using a touchscreen or a trackball. When the user input unit 190 receives a user input that selects a predetermined region, the image analyzing unit 110 may detect the selected region as a bloodstream region. The user input unit 190 will be explained below in detail with reference to FIG. 2.

The central axis determining unit 120 determines a central axis of the detected bloodstream region. That is, the central axis determining unit 120 determines any one straight line passing through the bloodstream region as a central axis of the bloodstream region. The central axis is a straight line for measuring a Doppler angle which is used to determine reliability of the color Doppler image. The central axis determining unit 120 may determine the central axis by using the bloodstream region displayed on the color Doppler image.

The central axis determining unit 120 may determine a straight line whose length is the greatest from among straight lines passing through the bloodstream region as the central axis. In detail, the central axis determining unit 120 may determine as the central axis a straight line whose length is the greatest from among straight lines obtained by connecting two arbitrary points included in the bloodstream region. Alternatively, since a straight line whose length is the greatest from among straight lines passing through a predetermined region is a straight line obtained by connecting two points located on edges of the predetermined region, the central axis determining unit 120 may determine the central axis by using two arbitrary points located on edges of the bloodstream region.

Alternatively, the central axis determining unit 120 may determine as the central axis any one of a plurality of straight lines passing through a central point of the bloodstream region. That is, the central axis determining unit 120 may map a plurality of pixels included in the bloodstream region to coordinates in a two-dimensional (2D) coordinate system and may determine a central point of the bloodstream region in the 2D coordinate system. Next, the central axis determining unit 120 may obtain a plurality of straight lines by rotating one straight line passing through the central point by 360° about the central point, and may measure lengths of the plurality of straight lines. The central axis determining unit 120 may determine a straight line whose length is the greatest from among the plurality of straight lines as the central axis of the bloodstream region.

Figure 6:
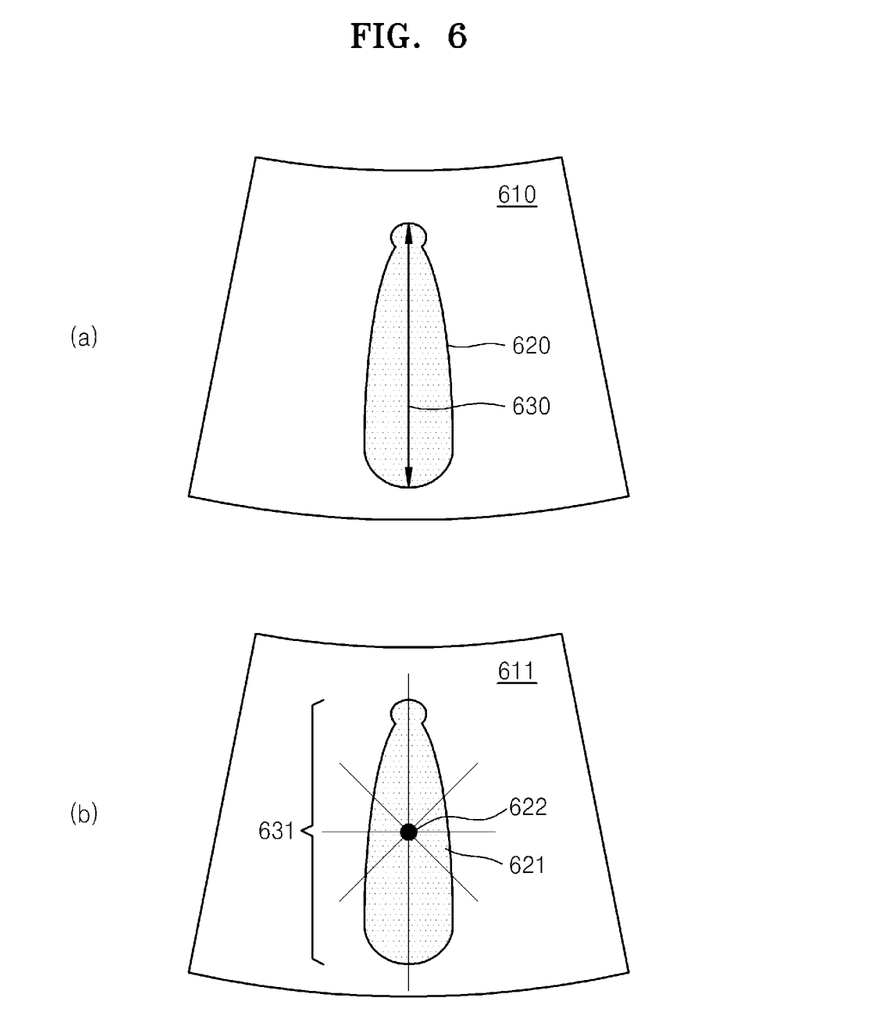
FIGS. 6A and 6B are views for explaining a process of determining a central axis of a bloodstream region, according to an embodiment of the present invention.

A process of determining a central axis which is performed by the central axis determining unit 120 will be explained below in detail with reference to FIGS. 6A-B.

The angle measuring unit 130 measures an angle between the central axis and a scan line used to obtain the color Doppler image. That is, the angle measuring unit 130 measures an angle between two straight lines by using information about the central axis obtained by the central axis determining unit 120 and information of the scan line used to obtain the color Doppler image.

As described above, as the angle measured by the angle measuring unit 130 decreases, reliability of the color Doppler image increases. Also, the angle measured by the angle measuring unit 130 may be equal to or greater than 0° and equal to or less than 90°. When the angle between the two straight lines exceeds 90° (and is equal to or less than 180°), the angle measuring unit 130 may use an angle obtained by subtracting 90° from the angle exceeding 90°.

The color Doppler image may be obtained by scanning the object along a plurality of scan lines, and the angle measuring unit 130 may measure the angle by using a scan line passing through the bloodstream region from among the plurality of scan lines. The angle measuring unit 130 may measure an angle between the central axis and a scan line passing through the central point of the bloodstream region from among the plurality of scan lines. Alternatively, the angle measuring unit may measure an angle between the central axis and a scan line whose length overlapping the bloodstream region is the greatest from among the plurality of scan lines.

The display unit 140 displays a variety of information along with an ultrasound image on a screen. That is, the display unit 140 may display the angle measured by the angle measuring unit 130 along with the color Doppler image on the screen. Also, the display unit 140 may display the central axis and the scan line which form the measured angle therebetween on the screen. Alternatively, the display unit 140 may visually display the bloodstream region distinguished from the color Doppler image or may display the central point of the bloodstream region on the screen.

The display unit 140 may display various information related to an ultrasound image by using colors instead of black and white. For example, the display unit 140 may display the angle measured by the angle measuring unit 130 by using various colors. In detail, the apparatus 100 may divide an angle from 0° to 90° into a plurality of angle sections, match the angle sections to respective colors, and previously store the angle sections and the colors which are matched to each other. The display unit 140 may display the angle in a color matched to the angle section, according to whether the angle measured by the angle measuring unit 130 corresponds to which angle section from among the plurality of the previously stored angle sections.

The apparatus 100 may divide an angle from 0° to 90° into one or more angle sections according to the reliability of the color Doppler image. Also, the display unit 140 may display on the screen the angle in a color matched to an angle section to which the measured angle corresponds, thereby visually distinguishably displaying the reliability of the color Doppler image, which will be explained below in detail with reference to FIG. 7.

Also, the display unit 140 may display an alarm message in graphics or text by using a pop-up window when the measured angle is not within a predetermined range in which the color Doppler image is considered to be reliable. That is, the display unit 140 may use a visual effect, for example, a pop-up window in order to guide a scan line.

The display unit 140 may include at least one of a liquid crystal display, a thin film transistor-liquid crystal display, an organic light-emitting diode display, a flexible display, and a three-dimensional (3D) display. Also, the apparatus 100 may include two or more display units 140 according to its type.

The display unit 140 may include a touchscreen that forms a layer structure with the user input unit 190 that receives an external input. That is, the display unit 140 may be used as both an output device and an input device, and in this case, the display unit 140 may receive a touch input by using a stylus pen or a body part.

Also, as described above, when the display unit 140 includes the touchscreen forming the layered structure, the display unit 140 may detect a position, an area, and a pressure of the touch input. Also, the touchscreen may detect not only a real touch but also a proximity touch.

The control unit 150 controls the image analyzing unit 110, the central axis determining unit 120, the angle measuring unit 130, and the display unit 140 included in the apparatus 100. That is, the control unit 150 may transmit/receive data between the elements or control one or more elements in order to guide a scan line.

Figure 2:
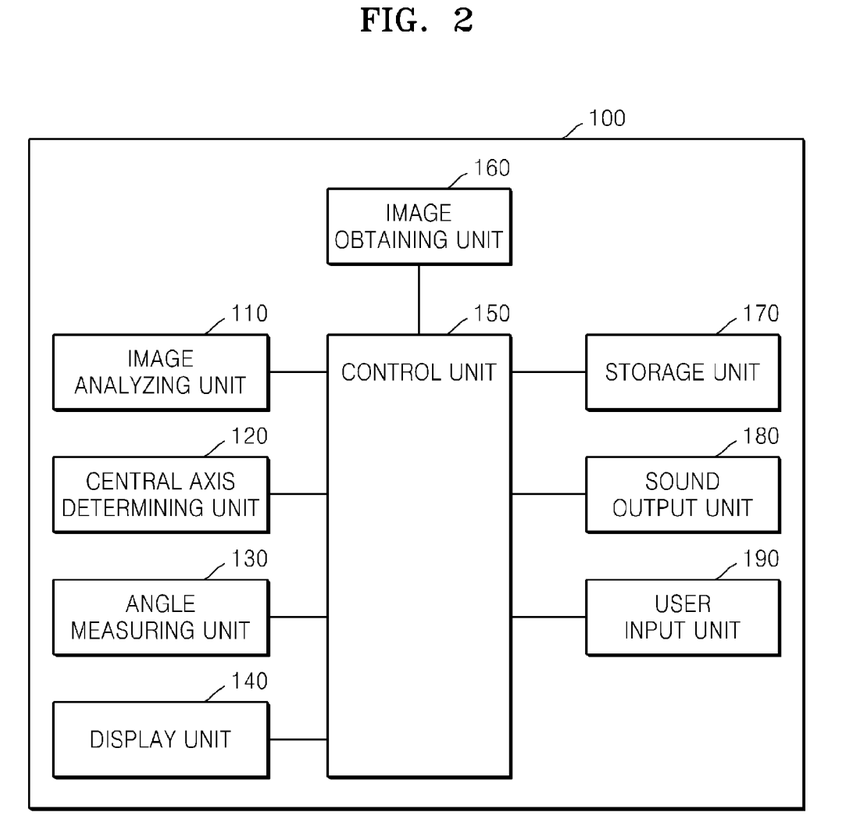
FIG. 2 is a block diagram illustrating an apparatus for guiding a scan line, according to another embodiment of the present invention.

FIG. 2 is a block diagram illustrating the apparatus 100 according to another embodiment of the present invention. The apparatus 100 may further include an image obtaining unit 160, the storage unit 170, a sound output unit 180, and the user input unit 190 in addition to the image analyzing unit 110, the central axis determining unit 120, the angle measuring unit 130, the display unit 140, and the control unit 150. The image analyzing unit 110, the central axis determining unit 120, the angle measuring unit 130, the display unit 140, and the control unit 150 have already been explained with reference to FIG. 1, and thus a detailed explanation thereof will not be given.

The image obtaining unit 160 obtains an ultrasound image by scanning an object. That is, the image obtaining unit 160 may obtain an ultrasound image by directly scanning the object, or may obtain an ultrasound image which has been previously stored.

The image obtaining unit 160 may include a transducer that emits an ultrasonic signal to the object and receives an echo signal reflected from the object. The image obtaining unit 160 may transmit the ultrasound image (in detail, the color Doppler image) obtained by scanning the object to the display unit 140 in real time, or may store the ultrasound image in the storage unit 170.

Alternatively, the image obtaining unit 160 may not scan the object by using the transducer, but may retrieve an ultrasound image previously stored in the storage unit 170. Also, the image obtaining unit 160 may receive an ultrasound image not only from the storage unit 170 but also from a hospital server through a picture archiving and communication system (PACS). When the image obtaining unit 160 obtains an ultrasound image which has been previously stored, a wired or wireless network technology may be used.

The storage unit 170 may store the ultrasound image and information about the ultrasound image. For example, the storage unit 170 may store along with the color Doppler image various information such as information about a bloodstream region included in the color Doppler image, information about a central axis of the bloodstream region, and information about an angle between the central axis of the image and a scan line.

Also, the storage unit 170 may previously store various information for guiding a scan line of the color Doppler image. For example, the storage unit 170 may divide an angle from 0° to 90° into one or more angle sections, and may store information about different colors matched to the angle sections. The storage unit 170 may store the information about the colors matched to the angle sections in a table.

The sound output unit 180 outputs audio data stored in the storage unit 170 when the object is diagnosed. Also, the sound output unit 180 may output an alarm message by using audio data when the angle between the central axis of the color Doppler image and the scan line is not within a predetermined range in which the color Doppler image is considered to be reliable. The sound output unit 180 may output audio data by using a speaker or a buzzer.

The user input unit 190 receives an input for controlling the apparatus 100 from the user. For example, the user input unit 190 may receive a user input that selects the bloodstream region in the color Doppler image as described above with reference to FIG. 1. Also, the user input unit 190 may receive various types of inputs for diagnosing the object, for example, a user input which increases or reduces a size of an ultrasound image displayed on a screen of the apparatus 100.

The user input unit 190 may include a keypad, a touchpad, a trackball, or a mouse. In particular, when the touchpad and the display unit 140 form a layer structure as described above, the user input unit 190 may include a touchscreen.

A method of guiding a scan line by using the color Doppler image in the apparatus 100 will now be explained with reference to FIGS. 3 and 4.

Figure 3:
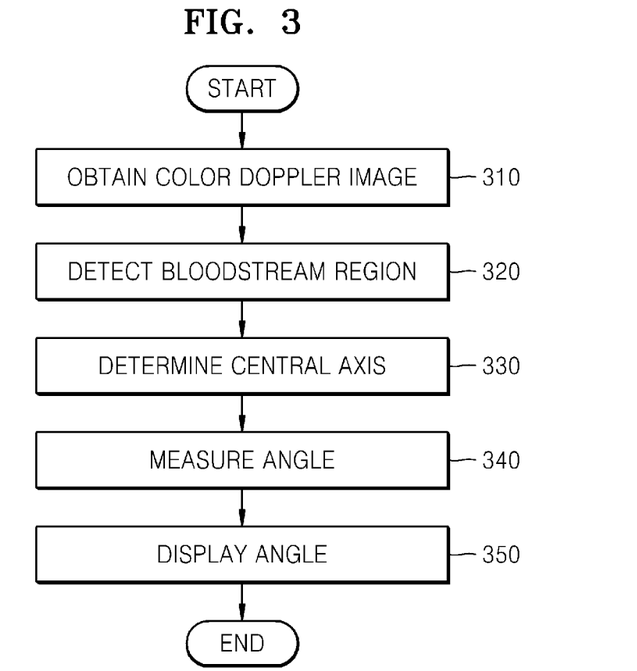
FIG. 3 is a flowchart illustrating a method of guiding a scan line, according to an embodiment of the present invention.
Figure 4:
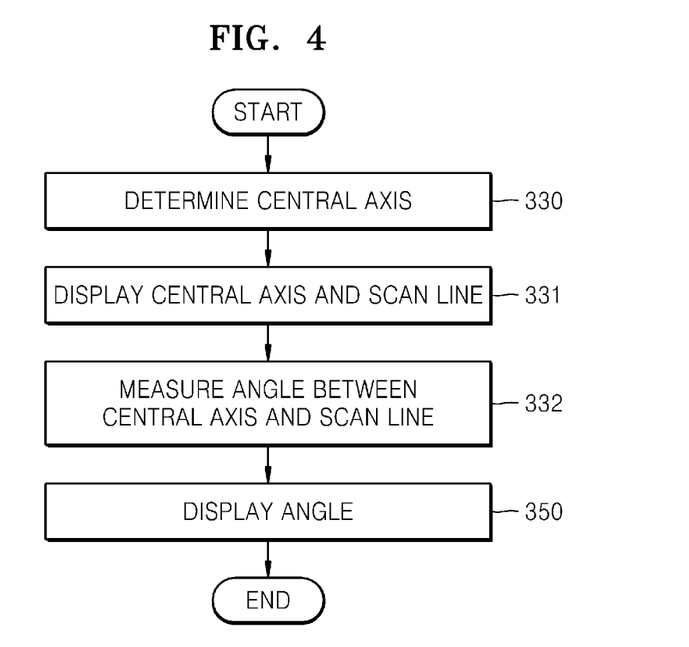
FIG. 4 is a flowchart illustrating a method of guiding a scan line, according to another embodiment of the present invention.

FIGS. 3 and 4 are flowcharts illustrating methods of guiding a scan line, according to embodiments of the present invention. The methods include operations sequentially performed by the image analyzing unit 110, the central axis determining unit 120, the angle measuring unit 130, the display unit 140, the control unit 150, the image obtaining unit 160, the storage unit 170, the sound output unit 180, and the user input unit 190 that are included or further included in the apparatuses 100 of FIGS. 1 and 2. Accordingly, although not described in FIGS. 3 and 4, descriptions which have been made for the elements with reference to FIGS. 1 and 2 may apply to the methods of FIGS. 3 and 4.

In operation 310, the apparatus 100 obtains a color Doppler image which is a cross-sectional image of an object. The image obtaining unit 160 included in the apparatus 100 may obtain the color Doppler image by directly scanning the object or may obtain the color Doppler image which has been stored in the storage unit 170 as described with reference to FIG. 2. The apparatus 100 may display the color Doppler image obtained in operation 310 on a screen.

In operation 320, the apparatus 100 detects a bloodstream region included in the color Doppler image. That is, the image analyzing unit 110 analyzes the color Doppler image obtained by the image obtaining unit 160 and detects the bloodstream region included in the color Doppler image.

As described with reference to FIG. 1, the image analyzing unit 110 may detect a color region including pixels with color values as the bloodstream region. Alternatively, the image analyzing unit 110 may detect the bloodstream region by using color values of a plurality of pixels included in the color Doppler image. Alternatively, the image analyzing unit 110 may detect a color region whose color value is within a predetermined range as the bloodstream region. Alternatively, the image analyzing unit 110 may detect a predetermined region selected by a user input received through the user input unit 190 as the bloodstream region.

In operation 330, the apparatus 100 determines a central axis of the bloodstream region. That is, the central axis determining unit 120 determines any one straight line passing through the bloodstream region detected by the image analyzing unit 110 as the central axis.

The central axis determining unit 120 may determine a straight line whose length included the bloodstream region is the greatest from among a plurality of straight lines passing through a central point of the bloodstream region as the central axis. Alternatively, the central axis determining unit 120 may determine a straight line whose length is the greatest from among straight lines obtained by connecting two arbitrary points included in the bloodstream region as the central axis.

In operation 340, the apparatus 100 measures an angle between the central axis and a scan line. That is, the angle measuring unit 130 may receive information about the central axis of the bloodstream region from the central axis determining unit 120, and may measure an angle between the central axis and a scan line used to obtain the color Doppler image.

In operation 340, the angle measuring unit 130 may measure an angle between the central axis of the bloodstream region and a scan line passing through the central point of the bloodstream region.

In operation 350, the apparatus 100 displays the angle measured by the angle measuring unit 130. That is, the display unit 140 displays the angle measured by the angle measuring unit 130 along with the color Doppler image on the screen.

The display unit 140 may display the angle measured by the angle measuring unit 130 on the screen in a color according to a previously determined range. That is, the display unit 140 may divide an angle from 0° to 90° into one or more angle sections, and may display the angle measured by the angle measuring unit 130 by using a color value matched to an angle section to which the angle corresponds.

According to the method of FIG. 3, information about reliability of the color Doppler image obtained by scanning the object may be visually obtained. Accordingly, a user of the apparatus 100 may conveniently determine whether to adjust a scan line by re-scanning the object according to reliability of the obtained color Doppler image.

FIG. 4 is a flowchart illustrating a method of guiding a scan line, according to another embodiment of the present invention. Operation 330 is the same as operation 330 of FIG. 3, and thus a detailed explanation thereof will not be given.

In operation 331, the apparatus 100 displays the central axis and the scan line on the screen. That is, the display unit 140 displays the central axis of the bloodstream region on the screen by using information about the central axis obtained by the central axis determining unit 120, and displays on the screen the scan line indicating an ultrasonic signal output by the image obtaining unit 160 to obtain the color Doppler image.

The display unit 140 may display on the screen a scan line passing through a central point of the bloodstream region from among a plurality of scan lines used to obtain the color Doppler image. Alternatively, the display unit 140 may display on the screen a scan line whose length overlapping the bloodstream region is the greatest from among a plurality of scan lines.

In operation 332, the apparatus 100 measures an angle between the central axis and the scan line on the screen. That is, the angle measuring unit 130 measures an angle between the central axis and the scan line displayed on the screen by the display unit 140. The angle measuring unit 130 may measure an angle equal to or greater than 0° and equal to or less than 90° from among angles formed between two straight lines.

In operation 350, the apparatus 100 displays the angle measured by the angle measuring unit 130 on the screen. The display unit 140 may display the angle in a color matched to the angle section on the screen according to whether the angle measured by the angle measuring 130 corresponds to which angle section from among a plurality of angle sections which are previously determined. That is, the display unit 140 may visually show reliability of the color Doppler image by displaying the measured angle in various colors.

Figure 5:
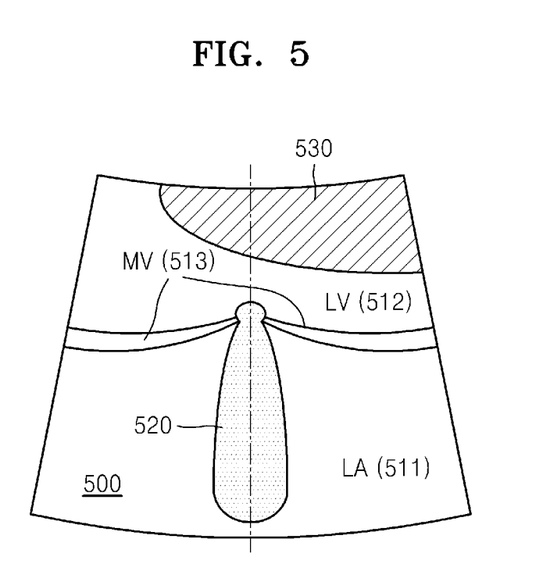
FIG. 5 is a view for explaining a process of detecting a bloodstream region, according to an embodiment of the present invention.

FIG. 5 is a view for explaining a process of detecting a bloodstream region, according to an embodiment of the present invention. FIG. 5 illustrates a left atrium (LA) 511, a left ventricle (LV) 512, and a mitral valve (MV) 513. Although a process of detecting a bloodstream region will be explained with reference to FIG. 5 illustrating the LA 511, the LV 512, and the MV 513, the present embodiment is not limited thereto.

Before explaining the process of FIG. 5, the LA 511, the LV 512, and the MV 513 will be explained first from the clinical point of view. When the LV 512 expands during diastole, the MV 513 is opened and blood is introduced from the LA 511 to the LV 512. Next, when the LV 512 contracts during systole, the MV 513 is closed and blood is introduced form the LV 512 to an aorta (not shown). Assuming that the MV 513 is damaged or a chordate tendineae connected to the MV 513 is damaged, since the MV 513 is not completely closed when the LV 512 contracts during systole, blood flows backward from the LV 512 to the LA 511. Such a disorder is called mitral regurgitation (MR).

In FIG. 5, in order to detect blood flowing backward from the LV 512 to the LA 511, the apparatus 100 obtains a color Doppler image 500 by scanning a part of a heart. The color Doppler image 500 of FIG. 5 includes a first region 520 which indicates blood flowing backward from the LV 512 to the LA 511 and a second region 530 which indicates blood flowing from the LV 512 to the aorta (not shown).

The apparatus 100 may match a velocity at which the object moves to a color value by using a color map, and may display the first region 520 and the second region 530 indicating flows of blood on the color Doppler image 500 by using colors. The apparatus 100 may determine the first region 520 and the second region 530 with color values from among a plurality of regions included in the color Doppler image 500 as color regions.

The first region 520 indicates blood flowing from the LV 512 to the LA 511, that is, flowing from up to down in the color Doppler image 500 of FIG. 5, whereas the second region 530 indicates blood flowing from the LV 512 to the Aorta, that is, flowing from down to up in the color Doppler image of FIG. 5. Accordingly, a flow of blood corresponding to the first region 520 and a flow of blood corresponding to the second region 530 are opposite to each other in terms of a direction. Accordingly, the apparatus 100 may display the first region 520 and the second region 530 of the color Doppler image 500 in different colors. For example, the apparatus 100 may display the first region 520 by using a first color (for example, red) and the second region 530 by using a second color (for example, blue), or vice versa.

Also, a user of the apparatus 100 may know a direction of a bloodstream of the object to be clinically measured. Accordingly, the apparatus 100 may obtain in advance information about a velocity of a bloodstream region to be detected according to whether a direction in which an ultrasound image is output to the object and a direction of the bloodstream are equal to or opposite to each other. For example, velocities of the first region 520 and the second region 530 may be, respectively, positive (+) and negative (−) values.

Also, the apparatus 100 may obtain in advance color information of a color (for example, red or blue) matched to a velocity of the bloodstream region by using a color map.

Accordingly, the apparatus 100 may detect the bloodstream region by using color information of the first region 520 and the second region 530 included in the color Doppler image 500 and the color information which has been previously stored. That is, since the first region 520 and the second region 530 have different color values (that is, different velocities), the apparatus 100 detects as the bloodstream region the first region 520 indicating a backward flow of blood to be measured from among the first region 520 and the second region 530 by using the color information of the bloodstream region which has been previously stored.

Alternatively, as described with reference to FIG. 1, the apparatus 100 may detect the bloodstream region by using color values of a plurality of pixels included in each color region. That is, the apparatus 100 may obtain an average color value of the pixels included in each color region, and may detect as the bloodstream region a color region whose average color value is within a predetermined range which has been previously stored.

Since a color displayed on the color Doppler image indicates a velocity of a bloodstream, the apparatus 100 may detect the bloodstream region by using velocity information instead of color information. That is, the apparatus 100 may detect as the bloodstream region a color region whose velocity is within a predetermined range which has been previously stored from among one or more color regions.

Blood flows backward farther away from the transducer in the first region 520, and blood flows closer to the transducer in the second region 530. Accordingly, the apparatus 100 may detect as the bloodstream region the first region 520 whose velocity is matched to a velocity at which blood flows farther away from the transducer. Since a velocity of the second region 530 which is matched to a velocity at which blood flows closer to the transducer exceeds a range of velocities of a bloodstream to be measured, the apparatus 100 does not detect the second region 530 as the bloodstream region.

FIGS. 6A and 6B are views for explaining a process of determining a central axis of a bloodstream region, according to an embodiment of the present invention. FIGS. 6A and 6B illustrate color Doppler images 610 and 611 including bloodstream regions 620 and 621, respectively.

In FIG. 6A, the apparatus 100 determines a straight line whose length included in the bloodstream region 620 is the greatest as a central axis 630. That is, the apparatus 100 may determine as the central axis 630 a straight line whose length is the greatest from among straight lines obtained by connecting two arbitrary points included in the bloodstream region 620. Also, as described above with reference to FIG. 1, the apparatus 100 may determine as the central axis 630 a straight line whose length is the greatest from among straight lines obtained by connecting two arbitrary points located on edges of the bloodstream region 620.

In FIG. 6B, the apparatus 100 may determine as the central axis 630 a straight line whose length overlapping the bloodstream region 621 is the greatest from among a plurality of straight lines 631 passing through a central point 622 of the bloodstream region 621.

That is, the apparatus 100 may map a plurality of pixels included in the bloodstream region 621 to coordinates in a 2D coordinate system, and may determine the central point 622 in the 2D coordinate system. Furthermore, the apparatus 100 may measure lengths of portions in which the plurality of straight lines 631 which pass through the central point 622 overlap the bloodstream region 621, and may determine a straight line whose length is the greatest as the central axis. The apparatus 100 may obtain the plurality of straight lines 631 by rotating one straight line by a predetermined angle about the central axis 622.

Figure 7:
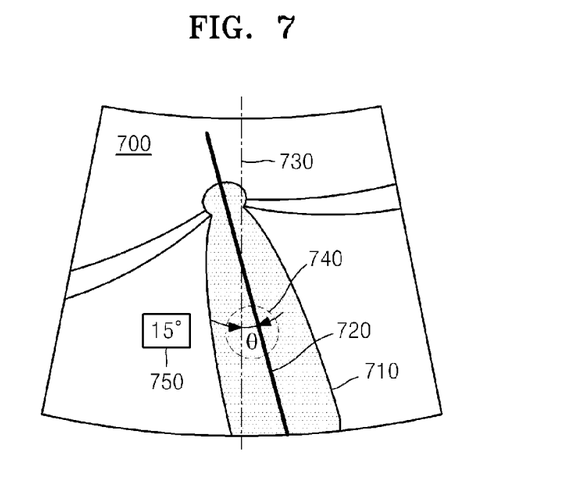
FIG. 7 is a view for explaining a process of displaying an angle between a scan line and a central axis on a screen, according to an embodiment of the present invention.

FIG. 7 is a view for explaining a process of displaying an angle between a scan line and a central axis on a screen, according to an embodiment of the present invention. A color Doppler image 700 of FIG. 7 includes a bloodstream region 710 and a central axis 720.

The apparatus 100 measures an angle 740 between the central axis 720 and a scan line 730. The apparatus 100 measures the angle 740 between the central axis 720 measured as described above with reference to FIGS. 1 and 6 and the scan line 730 used to obtain the color Doppler image 700.

Alternatively, the apparatus 100 may measure the angle 740 between the central axis 720 and the scan line 730 passing through the bloodstream region 710 from among a plurality of scan lines used to obtain the color Doppler image 700. In FIG. 7, the apparatus 100 measures the angle 740 between the central axis 720 and the scan line 730 whose length overlapping the bloodstream region 710 is the greatest from among the plurality of scan lines. Alternatively, the apparatus 100 may measure the angle 740 between the central axis 720 and a scan line passing through a central point (not shown) of the bloodstream region 710 from among the plurality of scan lines.

In FIG. 7, the apparatus 100 displays the angle 740 as an angle in an angle indication window 750 on the screen. The apparatus 100 may display the angle 740 on the screen by using any of various colors. The apparatus 100 may display the angle 740 in green when the angle 740 is equal to or greater than 0° and equal to or less than 20°, in yellow when the angle 740 is equal to or greater than 20° and equal to or less than 40°, and in red when the angle 740 is equal to or greater than 40° and equal to or less than 90°.

Accordingly, the apparatus 100 visually shows the angle 740 which affects reliability of the color Doppler image 700, thereby enabling the user to efficiently diagnose the object by using the color Doppler image 700. In FIG. 7, the apparatus 100 may indicate that the color Doppler image 700 is reliable by displaying an angle of 15° in green on the screen.

When the user of the apparatus 100 wants an angle less than 15° as the angle 740 (that is, when the user wants the color Doppler image having higher reliability), the apparatus 100 may adjust a position of the transducer that outputs an ultrasound image, to make the object re-scanned. However, when the user of the apparatus 100 determines that the color Doppler image 700 is sufficiently reliable, the apparatus 100 may continuously diagnose the object by using a current image.

FIGS. 8A through 8C are views for explaining a process of outputting an alarm message, according to an embodiment of the present invention.

FIG. 8A illustrates a color Doppler image 800 including a bloodstream region 810, a central axis 820, a scan line 830, an angle 840 between the central axis 820 and the scan line 830, and an angle in an angle indication window 850 displayed on a screen.

In FIG. 8A, the angle 840 between the central axis 820 and the scan line 830 is measured to be 45°. When it is determined that 45° is not within a predetermined range of angles, the apparatus 100 may output information that reliability of the color Doppler image 80 is low to the user. In other words, the apparatus 100 may divide an angle from 0° to 90° into a plurality of angle sections and may output an alarm message to the user when an angle equal to or greater than a threshold value is measured.

Figure 8:
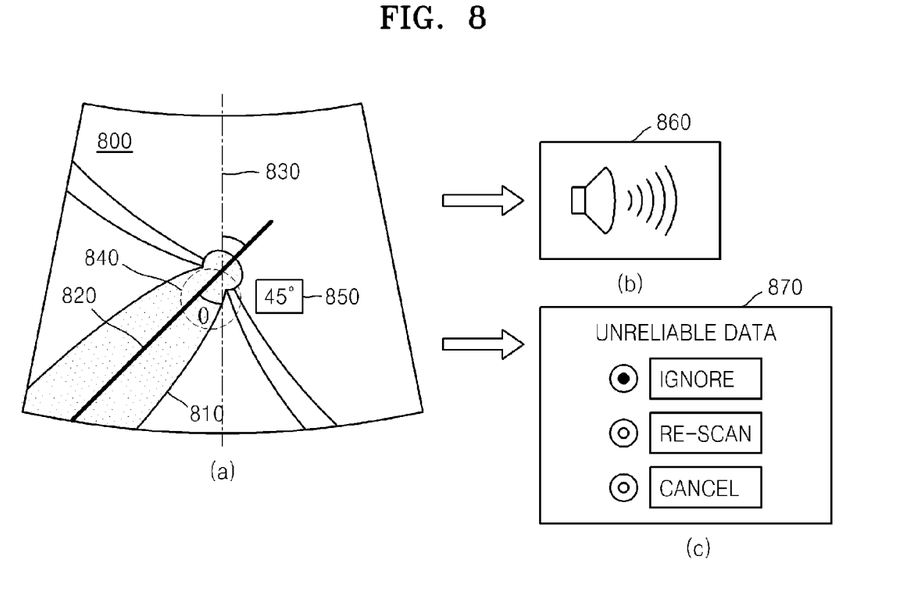
FIGS. 8A through 8C are views for explaining a process of outputting an alarm message, according to an embodiment of the present invention.

As described above with reference to FIG. 7, the apparatus 100 may display the angle 840 as the angle in the angle indication window 850 in red on the screen to warn the user. Also, the apparatus 100 may display not only the angle 840 but also a color of the central axis 820. In other words, in FIG. 7, the apparatus 100 may display the angle in the angle indication window 750 and the central axis 720 in green on the screen, and in FIG. 8, the apparatus 100 may display the angle in the angle indication window 850 and the central axis 820 in red on the screen.

Next, in FIG. 8B, as the apparatus 100 measures an angle that is equal to or greater than a threshold value, an alarm message is output to the user by using audio data (in 860). That is, the apparatus 100 may previously store various types of audio data such as an alarm call, a recorded voice, and various sound effects, and may output the audio data when an angle equal to or greater than a threshold value is measured (that is, when reliability is low).

In FIG. 8C, the apparatus 100 outputs a notification message by using a pop-up window 870. That is, the apparatus 100 may visually output a notification message in text or graphics.

In FIG. 8C, the apparatus 100 displays on the screen not only a text notification message indicating that the color Doppler image 800 which is a current image is not reliable, but also a pop-up window for selecting an item "Ignore Notification Message And Continuously Diagnose", an item "Re-scan Object", or an item "Cancel Current Operation and Return". When an input that selects any one of the items is received from the user, the apparatus 100 may perform an operation corresponding to the item.

The present invention may be embodied as a program executed in a computer, and may be implemented in a general purpose digital computer by using a computer-readable medium. Also, a structure of data used in the method may be recorded by using various units on a computer-readable medium. It should be understood that program storage devices, as may be used to describe storage devices containing executable computer code for operating various methods of the present invention, shall not be construed to cover transitory subject matter such as carrier waves or signals. Examples of the computer-readable medium include storage media such as magnetic storage media (e.g., read only memories (ROMs), floppy discs, or hard discs), optically readable media (e.g., compact disk-read only memories (CD-ROMs), or digital versatile disks (DVDs)), etc.

According to an apparatus and method for guiding a scan line, a user for diagnosing an object may easily visually recognize an angle between a scan line and a bloodstream region to be measured. That is, since the angle to be measured is distinguishably displayed on a screen in a color, the user may easily determine whether to adjust an angle and a direction of an ultrasonic signal. Accordingly, the reliability of a color Doppler image may be improved, and dependence of the color Doppler image on the user's skill may be reduced.

As described above, an angle between a scan line and a direction of a bloodstream may be minimized. Accordingly, the reliability of an obtained color Doppler image may be improved. Also, a dependence of the color Doppler image on a sonographer's skill may be reduced.

Since a user may recognize in real time an angle between a direction of a bloodstream and a scan line used to obtain a color Doppler image, the user may efficiently manage the reliability of the color Doppler image even when the user has little experience in diagnosing an object by using an ultrasound image. Also, the user may conveniently determine whether to re-scan the object according to the reliability of the color Doppler image.

While the present invention has been particularly shown and described with reference to exemplary embodiments thereof by using specific terms, the embodiments and terms have merely been used to explain the present invention and should not be construed as limiting the scope of the present invention as defined by the claims. The exemplary embodiments should be considered in a descriptive sense only and not for purposes of limitation. Therefore, the scope of the invention is defined not by the detailed description of the invention but by the appended claims, and all differences within the scope will be construed as being included in the present invention.

What is claimed is:

1. A method of guiding a scan line by using a color Doppler image, the method comprising:
   detecting a bloodstream region indicating a flow of blood from the color Doppler image;
   determining a central axis of the bloodstream region which is a straight line whose length is the greatest from among straight lines obtained by connecting arbitrary points included in the bloodstream region;
   measuring an angle between the central axis and the scan line used to obtain the color Doppler image; and
   displaying the angle on a screen.

2. The method of claim 1, wherein the measuring of the angle comprises:
   displaying the central axis and the scan line on the screen; and
   measuring the angle between the central axis and the scan line on the screen.

3. The method of claim 1, wherein the displaying of the angle on the screen comprises changing a color of the angle displayed on the screen according to whether the angle is within a predetermined range.

4. The method of claim 1, wherein the detecting of the bloodstream region comprises detecting the bloodstream region by using color information of one or more color regions included in the color Doppler image.

5. The method of claim 4, wherein the detecting of the bloodstream region comprises:
   obtaining an average color value of the one or more color regions by using color values of a plurality of pixels included in each of the one or more color regions; and
   detecting a color region whose average color value is within a predetermined range as the bloodstream region.

6. The method of claim 1, wherein the detecting of the bloodstream region comprises detecting as the bloodstream region a color region whose velocity is within a predetermined range from among a plurality of color regions included in the color Doppler image.

7. The method of claim 1, wherein the detecting of the bloodstream region comprises receiving a user input that selects a predetermined region included in the color Doppler image, and detecting the predetermined region as the bloodstream region.

8. The method of claim 1, further comprising outputting an alarm message when the angle is not within a predetermined range.

9. A method of guiding a scan line by using a color Doppler image, the method comprising:
   detecting a bloodstream region indicating a flow of blood from the color Doppler image;
   determining a central axis of the bloodstream region which is a straight line whose length included in the bloodstream region is the greatest from among a plurality of straight lines passing through a central point in the bloodstream region;

measuring an angle between the central axis and the scan line used to obtain the color Doppler image; and displaying the angle on a screen.

10. An apparatus for guiding a scan line by using a color Doppler image, the apparatus comprising:

an image analyzing unit that detects a bloodstream region indicating a flow of blood from the color Doppler image;

a central axis determining unit that determines a central axis of the bloodstream region which is a straight line whose length is the greatest from among straight lines obtained by connecting arbitrary points included in the bloodstream region;

an angle measuring unit that measures an angle between the central axis and the scan line used to obtain the color Doppler image; and a display unit that displays the angle on a screen.

11. The apparatus of claim 10, wherein the display unit displays the central axis and the scan line on the screen, and the angle measuring unit measures the angle between the central axis and the scan line on the screen.

12. The apparatus of claim 10, wherein the display unit distinguishably displays a color of the angle according to whether the angle is within a predetermined range.

13. The apparatus of claim 10, wherein the image analyzing unit detects the bloodstream region by using color information of a plurality of color regions included in the color Doppler image.

14. The apparatus of claim 13, wherein the image analyzing unit obtains an average color value of each of the one or more color regions by using color values of a plurality of pixels included in each of the one or more color regions, and detects a color region whose average color value is within a predetermined range as the bloodstream region.

15. The apparatus of claim 10, wherein the image analyzing unit detects as the bloodstream region a color region whose velocity is within a predetermined range from among a plurality of color regions included in the color Doppler image.

16. The apparatus of claim 10, further comprising a user input unit that receives a user input that selects a predetermined region included in the color Doppler image, wherein the image analyzing unit detects the predetermined region as the bloodstream region.

17. The apparatus of claim 10, wherein the apparatus outputs an alarm message when the angle is not within a predetermined range.

18. An apparatus for guiding a scan line by using a color Doppler image, the apparatus comprising:

an image analyzing unit that detects a bloodstream region indicating a flow of blood from the color Doppler image;

a central axis determining unit that determines a central axis of the bloodstream region which is a straight line whose length included in the bloodstream region is the greatest from among a plurality of straight lines passing through a central point of the bloodstream region;

an angle measuring unit that measures an angle between the central axis and the scan line used to obtain the color Doppler image; and a display unit that displays the angle on a screen.

\* \* \* \* \*